United States Patent [19]

Resnick

[11] 4,385,067
[45] May 24, 1983

[54] FUNGICIDAL NITRILOMETHYLIDYNE PHENYL-ACRYLATES AND METHOD OF USE

[75] Inventor: Bruce M. Resnick, West Paterson, N.J.

[73] Assignee: GAF Corporation, New York, N.Y.

[21] Appl. No.: 250,465

[22] Filed: Apr. 3, 1981

[51] Int. Cl.³ .............................................. A01N 37/06
[52] U.S. Cl. ..................................... 424/314; 560/138
[58] Field of Search ................. 424/313, 314; 560/138

[56] References Cited

U.S. PATENT DOCUMENTS 4,260,809 4/1981 Gruber et al. ...................... 560/138

*Primary Examiner*—Allen J. Robinson
*Attorney, Agent, or Firm*—James Magee, Jr.; Marilyn J. Maue

[57] ABSTRACT

A broad spectrum fungicide having the formula:

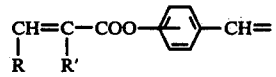

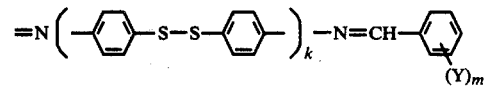

wherein Y is acrylate, methacrylate, hydroxy, methoxy, halo, or a halogenated methyl group; k has a value of 0 or 1; m has a value of from 0 to 2, and R and R' are each independently hydrogen or methyl and mixtures of said acrylates as well as the method of their application to plants for the control of fungi infestation.

11 Claims, No Drawings

FUNGICIDAL NITRILOMETHYLIDYNE PHENYL-ACRYLATES AND METHOD OF USE

This invention relates to fungicides, and more particularly to broad spectrum fungicides as eradicants and protectants against infestation by plant pathogens.

The effective mycological inhibition evidenced by differentiated chemical species is a complex function of a number of variables including specific activity, resistance to weathering, the type of plant treated, the degree of infestation and varying levels of phytotoxicity. Ecological considerations have barred the use of many effective fungicides because of their persistent residues and toxicity to humans by prolonged ingestation of food crops. To be commercially acceptable current fungicides must leave no toxic residue, they must be easily handled, operate consistently within a spray schedule and be economical to prepare. The foregoing requirements limit the selection of totally acceptable, effective fungicidal agents to a relatively small group of compounds. While many of the available materials comprise complex molecules of specific functionality, most are difficult or expensive to prepare and many of these materials, while effective against one fungicides species, e.g. rusts, are not effective against other species, e.g. mildew or anthracnose. Such highly specialized fungicides necessitate the use of several sprays for controlling multifungicidal infestation; thus, increasing the amount of residue remaining on the plant or in the soil.

Accordingly, it is an object of the present invention to provide an effective broad spectrum fungicide for the control of mildews, rusts and anthracnose, suitable for application to plants and particularly suitable for food crops since, under normal conditions, these compounds leave no toxic residue.

It is another object of the present invention to provide effective mycological agents which are economical to prepare and convenient to use.

In accordance with the present invention, there is provided a broad spectrum, fungicidally effective compound having the formula:

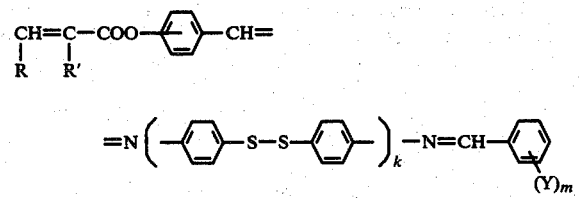

wherein Y is acrylate, methacrylate, hydroxy, methoxy, halo, or a halogenated methyl group; k has a value of 0 or 1; m has a value of from 0 to 2; and R and R' are each independently hydrogen or methyl. It is also to be understood that mixtures of the above compounds may be employed in the operation of the present invention.

In general the esters of the present invention are prepared by reacting hydrazine hydrate with hydroxybenzaldehyde in acid solution to precipitate bis(phenol) dinitrilomethylidyne having the formula

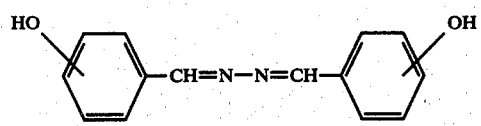

as an intermediate and reacting in basic solution said intermediate with at least 2 mole equivalents of the desired acryloyl halide, the chloride or bromide, having the formula

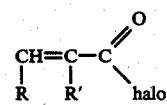

to provide the corresponding product having the formula:

The corresponding monoacrylate phenols of these compounds are similarly prepared, except that only one mole equivalent of the acryloyl halide is employed. The corresponding monoacrylate methoxy phenols are also prepared in a two-step procedure whereby a hydroxy benzaldehyde is reacted with an excess of hydrazine hydrate. The hydroxy phenyl hydrazone is then reacted with a second substituted benzaldehyde to yield the unsymmetrical nitrilomethylidyne phenol.

The pH in the second stage of the reaction is maintained from about 5 to 6.8 with a mineral or organic acid, preferably with acetic acid or a mixture of acetic acid and sodium acetate.

The diacrylate disulfides of the invention can be prepared by reacting bis 4,4'-(phenol nitrilomethylidyne phenyl) disulfide with at least 2 molar equivalents of the above named acryloyl halide.

The above reactions are beneficially carried out in the presence of a solvent; for example, a liquid compound selected from the group consisting of methylene chloride, ethanol, propanol, butanol, toluene, xylene, benzene or a liquid aliphatic hydrocarbon such as heptane, octane, cyclohexane, or any other conventional inert organic solvent. The reactions are effected at a temperature of from about −25° C. to about 120° C. under atmospheric pressure for a period of from about 0.5 to about 4 hours total reaction time. The resulting product is filtered, washed with water to extract the halide salt by-product, dried over a desiccant, e.g. magnesium sulfate, filtered to remove desiccant and vacuum distilled to remove solvent.

The product is recovered in a high yield and purity, for example, there is obtained at least 80% conversion of which about 80% is the desired product.

Since the compounds of the present invention are known they can be obtained by other known methods of preparation or by methods which will become apparent to those skilled in the art from the above discussion of desirable compounds and reaction conditions.

Examples of phenylnitrilomethylidyne phenol reactants which can be used in the process for preparing the compounds of the present invention are those having the formula

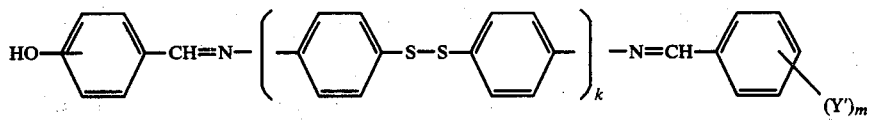

wherein m and k are as defined above and Y' is a hydroxy, methoxy, halo or halogenated methyl group.

The unsaturated acyl halide of the above reaction is defined as having the structure

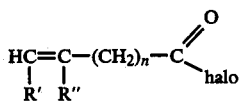

wherein R' is hydrogen, chlorine or bromine; R" is hydrogen or methyl; n has a value of 0 to 2 and halo is chlorine or bromine. Of this group acryloyl chloride and methacryloyl chloride are most preferred.

The esters of the present invention effect inhibition of widely variant plant pathogens and may be generally used in the control of infestations on many species of plants by application prior to infestation as a protectant or after infestation to retard established growth. Although the present products may be applied in full strength, directly to a plant or plant part for economy and better distribution, the product is preferably applied in diluted form as a liquid solution or dispersion or as particulate solid or a dust. Suitable liquid carriers for the present products include water and organic solvents such as isopropanol, ethyleneglycol, acetone, benzene, toluene, polyethylene glycol, polypropylene glycol, and other conventional inert carriers. Exemplary of the solid carriers suitably employed with the present products are talc, bentonite, diatomaceous earth clays, and the like.

The concentration of the active fungicide varies with the species of plant treated, the mycological species sought to be controlled, climatic conditions and the particular fungicide employed; however, the present products are usually applied in a concentration of between about 5 and about 300 parts per million, preferably between about 20 and about 200 parts per million, applied to provide coverage of from about 1 to about 30 lbs. per acre, preferably about 3 to about 25 lbs. per acre. In certain cases involving a persistent or heavy fungicidal infestation, it may be desirable to employ solutions up to 500 ppm of the present fungicides.

The fungicidal compositions of the present invention may also be applied to or compounded in or with other substrates susceptible to fungal infestation including wood, paper, leather textiles etc.; however their preferred utility is expressed in the field of agriculture, and particularly in the control of plant pathogens as by foliar application as a liquid spray or dust either to growing crops or processed agricultural products, e.g. picked fruit or vegetables. The present products may also find utility as bacteriocides in household or commercial washing or cleansing solutions.

The fungicidal products can be formulated and applied with carrier or they may be incorporated in available formulations containing other agriculturally active agents such as plant growth regulators, insecticides, fertilizers or herbicides, as are presently marketed. In all cases, the fungicidal compositions of this invention are used in fungicidally effective amounts in the desired formulation. Liquid compositions containing the present fungicides can be applied to plants by spraying to drench, by misting or by immersing picked fruit or vegetables in a fungicidal solution. Also wrappings for fruits and vegetables can be impregnated with the present fungicide/carrier composition to prevent rot or decay during shipment and distribution.

If desired, the present fungicidal compositions may include any of the conventional adjuvants such as surfactants, thickening agents, or sticking agents.

Having generally described the present invention, reference is now had to the accompanying examples which illustrate preferred embodiments but which are not to be construed as limiting the scope of the invention as set forth in the foregoing description and in the appended claims. All amounts and proportions recited in the following examples are by weight unless otherwise indicated.

EXAMPLE A

This example illustrates a method for synthesizing dinitrilomethylidyne bis(phenylacrylate)

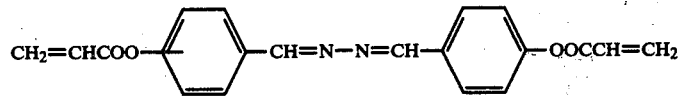

of the present process and is representative of the method for preparing the other fungicidal species of this invention.

To a mixture of 4.9 g of p-hydroxybenzaldehyde in 20 ml of ethanol was added 1 g of hydrazine hydrate, 0.25 ml of acetic acid and 0.1 ml of 10% sodium acetate. The mixture was stirred and refluxed for about 1 hour during which precipitation of the corresponding dinitrilomethylidyne bis(phenol) occurs. After cooling to room temperature, the solid was collected, dried and weighed 3.95 g (82% yield) of intermediate product. The intermediate was then neutralized with 30 ml of water containing 2 equivalents of NaOH. To this neutralized solution was added 2.8 g acryloyl chloride in 50.0 ml methylene chloride and the mixture slurried for 1.5 hours at 25°-30° C. The solid product is filtered off, then washed with water, dried over magnesium sulfate and weighed at 3.25 g (78% yield) of product. The product was identified by spectroscopic analysis.

EXAMPLE B

Preparation of unsymmetrical dinitrilomethylidynephenyl mono acrylates, e.g. 4-methoxyphenyl-dinitrilomethylidyne-2'-phenylacrylate, having the formula:

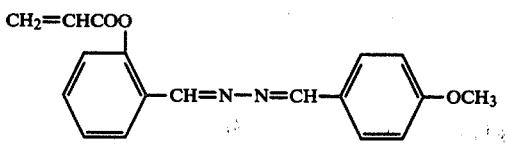

To a glass flask was added 12.2 g of dinitrilomethylidyne-2-phenol, prepared by refluxing 24.4 g (0.2 moles) of salicylaldehyde with 75.5 g (1.50 moles) of hydrazine monohydrate dissolved in 500 ml. absolute alcohol for 2 hours with agitation, cooling, evaporating under reduced pressure and filtering to separate 17 g. of salicylaldehyde hydrazone (m.p. 96°–97° C.). This compound, together with 13.6 g. of p-methoxybenzaldehyde was dissolved in 180 ml of absolute ethanol containing 0.5 ml of 10% aqueous sodium acetate and 10 ml of acetic acid. The resulting mixture was refluxed for one hour and cooled to an ice bath to precipitate the corresponding 2-phenol dinitrilomethylidyne-4'-methoxybenzene intermediate.

The intermediate (5 g.) was then added to a solution of 350 ml acetone in 200 ml of water containing 0.79 g. of sodium hydroxide and warmed to dissolve the intermediate compound whereupon 1.78 g. of acryloyl chloride was added dropwise with stirring at 35°–40° C. and the solution neutralized to a pH of 7 with 2 ml of 10% sodium hydroxide. The volume of the resulting solution was reduced to half and product precipitated. The precipitate was collected by vacuum filtration to provide 2.3 g. (40% yield) of product (m.p. 87.5°–88.5° C.).

In the above example, 4-chlorobenzaldehyde or 3-trifluoromethylbenzaldehyde can be substituted for 4-methoxybenzaldehyde to provide the corresponding 4-chlorophenyl-dinitrilomethylidyne-2-hydroxybenzene intermediate, i.e.

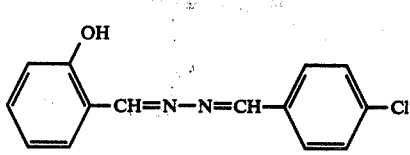

and, subsequently, the corresponding 4-chlorophenyl-dinitrilomethylidyne-2-phenyl acrylate.

EXAMPLE C

Preparation of 2,2'[dithio bis(4,1-phenylenenitrilomethylidyne)bis-phenylacrylate], i.e.

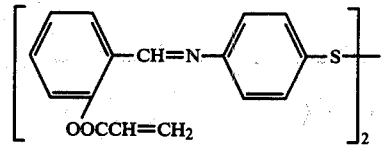

To a neutralized aqueous solution of 2,2'[dithio bis(4,1-phenylenedinitrilomethylidyne) phenol], i.e.

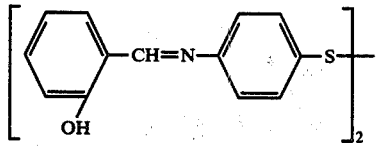

(prepared according to the process described in Chemical Abstracts, Volume 63, item 13125f) was added 2 molar equivalents of acryloyl chloride. The mixture was stirred and reacted and recovered in the manner described in Example A to produce the disulfide product in 70% yield.

When one molar equivalent of acryloyl chloride is employed above, the corresponding monoacrylate having the formula

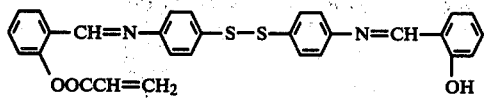

is produced.

It is to be understood that in any of the above examples acryloyl bromide can be substituted for acryloyl chloride to provide identical products. Also in the above examples, a methacryloyl chloride or bromide can be substituted to produce the corresponding phenyl methacrylates of the above named products.

EXAMPLE 1

Bean rust (*Uromyces phaseoli*) is representative of a large number of obligate parasites whose prolificacy in generating new parasitic races has frequently frustrated efforts to control them by breeding for disease resistance. The present tests were made with separate aqueous solutions each containing 260 ppm the compounds shown in Table II on Pinto beans grown in 2.5 inch pots for 9 to 12 days by a combination of foilage spray and systemic protection from soil applications. In the test 21 ml of a 520 ppm formulation (equivalent to 25 lb/acre) was poured on the surface of the soil. At the same time the foilage was sprayed with 100 ml of the aqueous solutions containing 260 ppm of the compounds shown in Table I while plants were rotating on a turntable. After the spray deposit had dried, the plants were atomized with a suspension of uredospores (summer spore stage) and placed in a moist chamber at 70° F. for 24 hours. After 7 to 9 days the severity of pustule formation was rated in % control, as compared to untreated controls. The results are reported in following Table I.

TABLE I

| Test Compound | Chemical Name | % Control of Rust Infestation |
|---|---|---|
| 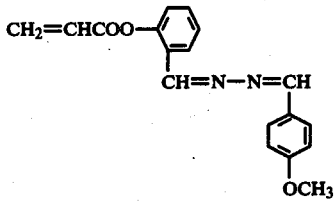 | p-methoxyphenyl-dinitrilomethyl-idyne-o'-phenyl-acrylate | 90 |
| 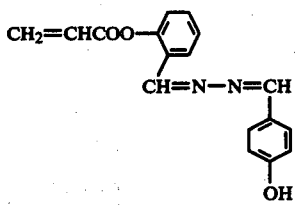 | p-hydroxyphenyl-dinitrilomethylidyne-o'-phenylacrylate | 30 |
| 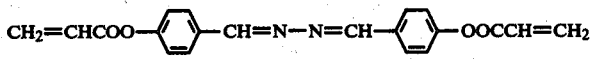 | dinitrilomethyl-idyne-bis(4,4'-phenylacrylate) | 80 |

Substitution of 260 ppm of the following compounds in the present example provide at least 50% control of bean rust.

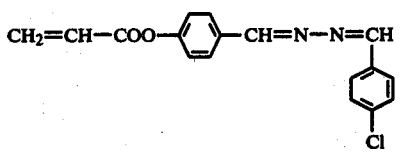

and

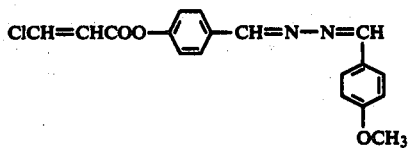

The above compounds did not exhibit systemic activity; hence foliar application is recommended.

EXAMPLE 2

Cucumber anthracnose (*Colletotrichum lagenarium*) is a representative of leaf blights caused by the *Fungi imperfecti*. Tests were made on cucumber plants grown in 2.5 inch pots for 9-12 days by a combination of foilage spray. In the test, the foilage was sprayed with 100 ml of a 250 ppm aqueous formulation of the compounds reported in Table II as described below. After the spray deposit had dried, the treated plants were inoculated with a suspension of anthracnose conidia in water and placed in a moist chamber at 24° C. for 24 hours. Four days after inoculation, the number of lesions were counted, and the rating was based on % control.

TABLE II

| Test Compound | % Control of Anthracnose Infestation |
|---|---|
| 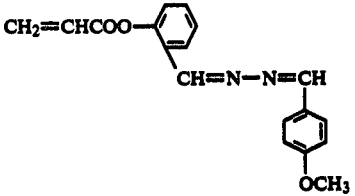 | 100 |
| 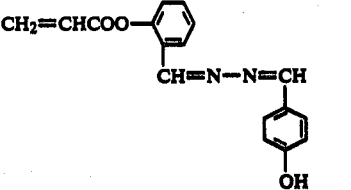 | 30 |

TABLE II-continued

| Test Compound | % Control of Anthracnose Infestation |
|---|---|
| 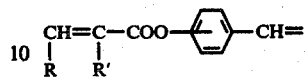 | 90 |

EXAMPLE 3

The general procedures described the above examples 1 and 2 were repeated for the most active compound (at various lower concentrations reported in Table III. Control of the rust and anthracnose, at various fungicidal concentration levels are as follows.

TABLE III

| Test Compound | Pathogen | % Control of Pathogen | | | | |
| | | 130 ppm | 65 ppm | 33 ppm | 16 ppm | 8 ppm |
|---|---|---|---|---|---|---|
| CH₂=CHCOO–⟨⟩–CH=N–N=CH–⟨⟩–OCH₃ | R* | 100 | 80 | 80 | — | — |
| | A* | 100 | 40 | — | — | — |
| [CH₂=CHCOO–⟨⟩–CH=N]₂ | R | 100 | 100 | 90 | 80 | 80 |
| | A | 90 | 40 | 40 | — | — |

*R = rust; A = anthracnose

As shown in the above tables the most preferred concentration levels of the present fungicidal compounds fall within the range of between about 30 and about 300 ppm. Other compounds, included within the scope of the present invention may require higher concentrations to achieve maximum effectiveness, e.g., concentrations of up to about 500 ppm. The present compounds are advantageously used on edible crops since they leave no toxic residue and have no systemic effect beyond 2 weeks following application. These properties make the present fungicidal compounds ideal for treatment of picked fruit and vegetables to prevent spoilage in shipment and storage.

It is to be understood that many variations and modifications of the above examples will become apparent to those skilled in the art and are considered to be in the scope of the invention. For example, the present fungicides may be incorporated into solid carriers such as clay, talc, pumice, or bentonite to provide compositions which may be applied either to infested areas on the plant or to areas which may be subjected to infestation. They may also be dissolved in liquified gases such as methyl chloride and applied as aerosol sprays containing the solution. Also, any of the above indicated nitrilomethylidyne phenylacrylates which are not illustrated in the above examples can be substituted therein to provide similar fungicidal control.

I claim:

1. The method of inhibiting growth of plant pathogenic fungi which comprises exposing said fungi to a fungicidal quantity of a compound having the formula

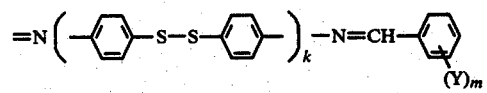

wherein Y is acrylate, methylacrylate, hydroxy, methoxy, halo, or a halogenated methyl group; k has a value of 0 or 1; m has a value of from 0 to 2 and R and R' are each independently hydrogen or methyl and mixtures of said compounds.

2. The method of claim 1 wherein said compound is applied to a plant in admixture with an inert carrier.

3. The method of claim 2 wherein R of the compound is hydrogen.

4. The method of claim 3 wherein R' of the compound is methyl.

5. The method of claim 3 wherein R and R' of the compound are both hydrogen.

6. The method of claim 5 wherein k of the compound is zero.

7. The method of claim 5 wherein the fungicide is dinitrilomethylidyne bis(phenylacrylate).

8. The method of claim 5 wherein the fungicide is p-methoxyphenyl-dinitrilomethylidyne-o'-phenylacrylate.

9. The method of claim 2 wherein the compound is employed with an aqueous carrier in a concentration of between about 30 and about 500 ppm.

10. The method of claim 9 wherein the fungus is plant rust.

11. The method of claim 9 wherein the fungus is anthracnose.

* * * * *